(12) United States Patent
Geigle et al.

(10) Patent No.: US 11,397,144 B2
(45) Date of Patent: Jul. 26, 2022

(54) FILM STRUCTURE PUNCTURE TESTING TOOL AND METHOD

(71) Applicant: Sargento Foods Inc., Plymouth, WI (US)

(72) Inventors: Mallory Geigle, Elkhart Lake, WI (US); Todd Purkey, Elkhart Lake, WI (US); Kevin Heidemann, Elkhart Lake, WI (US)

(73) Assignee: Sargento Foods Inc., Plymouth, WI (US)

( * ) Notice: Subject to any disclaimer, the term of this patent is extended or adjusted under 35 U.S.C. 154(b) by 212 days.

(21) Appl. No.: 17/003,126

(22) Filed: Aug. 26, 2020

(65) Prior Publication Data

US 2022/0065762 A1    Mar. 3, 2022

(51) Int. Cl.
| | |
|---|---|
| *G01N 33/00* | (2006.01) |
| *G01N 3/42* | (2006.01) |
| *G01N 3/04* | (2006.01) |
| *B65D 77/20* | (2006.01) |
| *B65B 7/28* | (2006.01) |

(52) U.S. Cl.
CPC ............ *G01N 3/04* (2013.01); *B65B 7/2878* (2013.01); *B65D 77/20* (2013.01); *G01N 33/00* (2013.01); *G01N 2033/0081* (2013.01); *G01N 2203/0282* (2013.01)

(58) Field of Classification Search
CPC .. G01N 3/04; G01N 33/00; G01N 2033/0081; G01N 2203/0282; B65B 7/2878; B65B 9/04; B65D 77/20; B65D 81/2084; B65D 25/10; B65D 1/34; B65D 77/2052; B32B 27/00; B31B 50/81
See application file for complete search history.

(56) References Cited

U.S. PATENT DOCUMENTS

| | | | |
|---|---|---|---|
| 6,777,047 B1 * | 8/2004 | Tatarka | ................... C08L 23/10 428/515 |
| 2003/0022010 A1 * | 1/2003 | Deeb | ......................... B32B 7/12 428/517 |
| 2003/0118804 A1 * | 6/2003 | Bedingham | .............. B29D 7/01 62/313 |

OTHER PUBLICATIONS

"Puncture Resistance Testing On Plastic Film"; YouTube video uploaded by AMETEKSTC on Jun. 14, 2019; https://www.youtube.com/watch?v=5c2XFW1CW_w.

* cited by examiner

*Primary Examiner* — Brandi N Hopkins
(74) *Attorney, Agent, or Firm* — Boyle Fredrickson, SC

(57) ABSTRACT

A film structure puncture testing tool for testing the resistance to puncturing of a film structure for a product package and a method for analyzing film structures resistance to puncturing.

17 Claims, 5 Drawing Sheets

FILM STRUCTURE PUNCTURE TESTING TOOL AND METHOD

FIELD OF THE INVENTION

The present disclosure relates to a comparative and replicable testing method that provides for the puncture testing of film structures that are used to seal product packages.

BACKGROUND OF THE INVENTION

Testing a film structure's resistance to puncturing has previously involved the use of a testing probe. Such probe testing systems are typically expensive to purchase and have maintenance fees attached to them.

SUMMARY OF THE INVENTION

In one construction, the disclosure provides a film puncture testing tool for testing resistance to puncturing of a film structure for a product package. The film puncture testing tool includes a tray mold insertable into a product package and including one slot and an insert terminating in an end, the insert being positioned in the slot in an orientation with the end extending outwardly of the slot so that a film structure to be tested can be sealed to the product package over the mold and the insert.

In another construction, the disclosure provides method for testing the resistance of a film structure on product package to puncturing. The method including the steps of inserting a tray mold having a slot into a product package, inserting an insert into the slot, the insert having a portion that extends outwardly from the slot to simulate a rigid object in the product package and covering the tray mold and the insert with a film structure to be tested.

In another construction, the disclosure provides a method for analyzing the puncture resistance of a film structure sealed to a product package using a sealer. The method including the steps of inserting a tray mold having a slot into a product package, the slot having a height, inserting an insert having a height greater than the height of the slot into the slot so that the insert extends outwardly from the slot, sealing a film structure to the product package over the mold and the insert using a sealer used to produce the product package and analyzing the test film structure to determine the resistance to puncturing of the film structure.

In another construction, the disclosure provides a method for testing the resistance of a film structure on product package to puncturing. The method including the steps of inserting a tray mold into a product package, the tray mold having at least one insert extending outwardly therefrom to simulate a rigid object in the product package and covering the tray mold and the insert with a film structure to be tested.

Other aspects of the disclosure will become apparent by consideration of the detailed description and accompanying drawings.

DETAILED DESCRIPTION

Before any constructions of the disclosure are explained in detail, it is to be understood that the disclosure is not limited in its application to the details of construction and the arrangement of components set forth in the following description or illustrated in the following drawings. The disclosure is capable of other constructions and of being practiced or of being carried out in various ways.

With reference to FIGS. 1-6, there is shown a tray mold 10 shaped to fit into a product package 12. The figures illustrate two tray molds in one product package 12, however, one tray mold can also be utilized. The tray mold 10 is preferably manufactured from plastics (including, but not limited to, PLA, Poly Carbonate, ABS, PETG, Nylon, ULTEM) using a 3d printing process, however, other materials and processes such as metals (including, but not limited to, aluminum, stainless steel and titanium) can also be utilized. The tray mold 10 can fill the entire product package 12 as shown, however, it can also be designed to fill only a portion of the product package 12.

The tray mold 10 includes at least one and preferably a plurality of slots 14. The slots 14 as shown are rectangular, however, other shapes can also be utilized such as including, but not limited to round, square, oval, hexagonal, octagonal.

Figure 1:
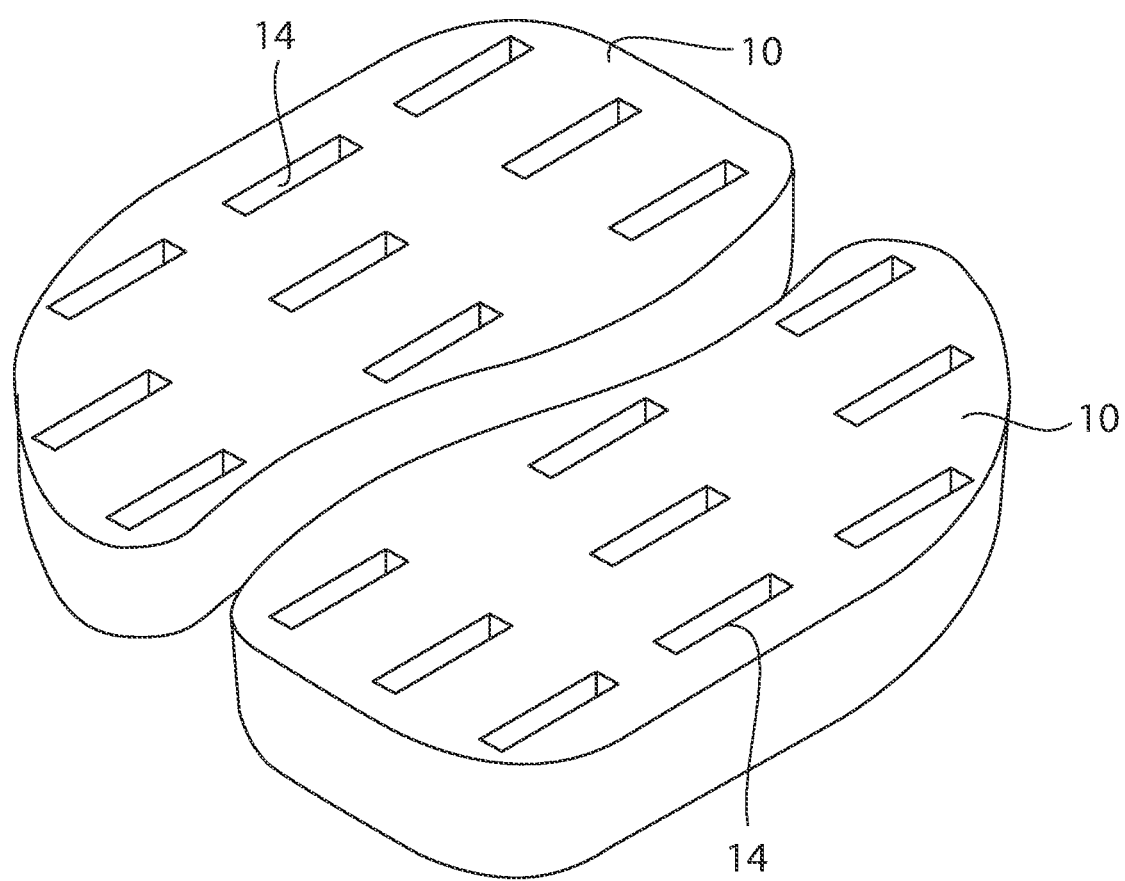
FIG. 1 is a perspective view of a tray mold.
Figure 2:
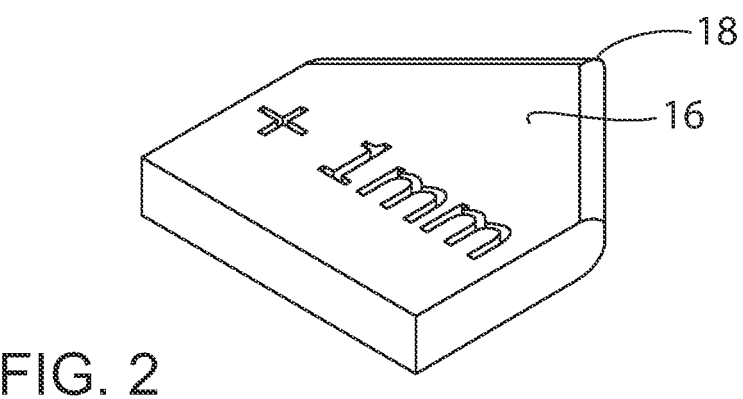
FIG. 2 is a perspective view of a 1 mm insert.
Figure 3:
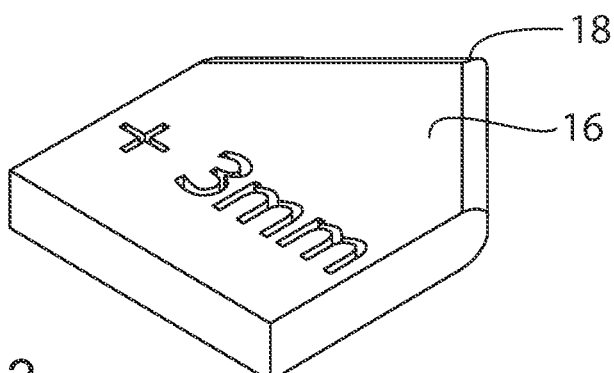
FIG. 3 is a perspective view of a 3 mm insert.
Figure 4:
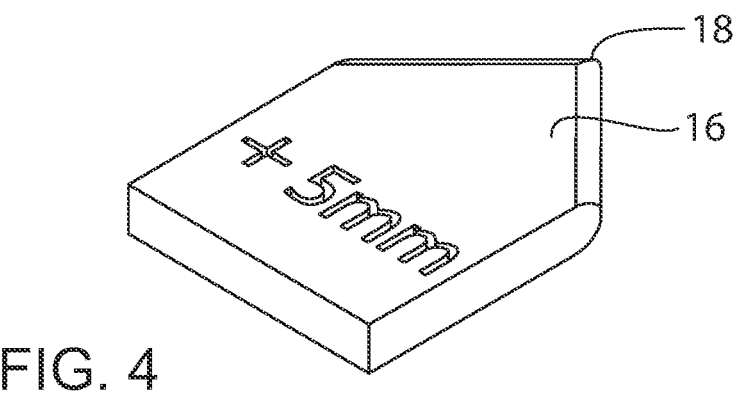
FIG. 4 is a perspective view of a 5 mm insert.
Figure 5:
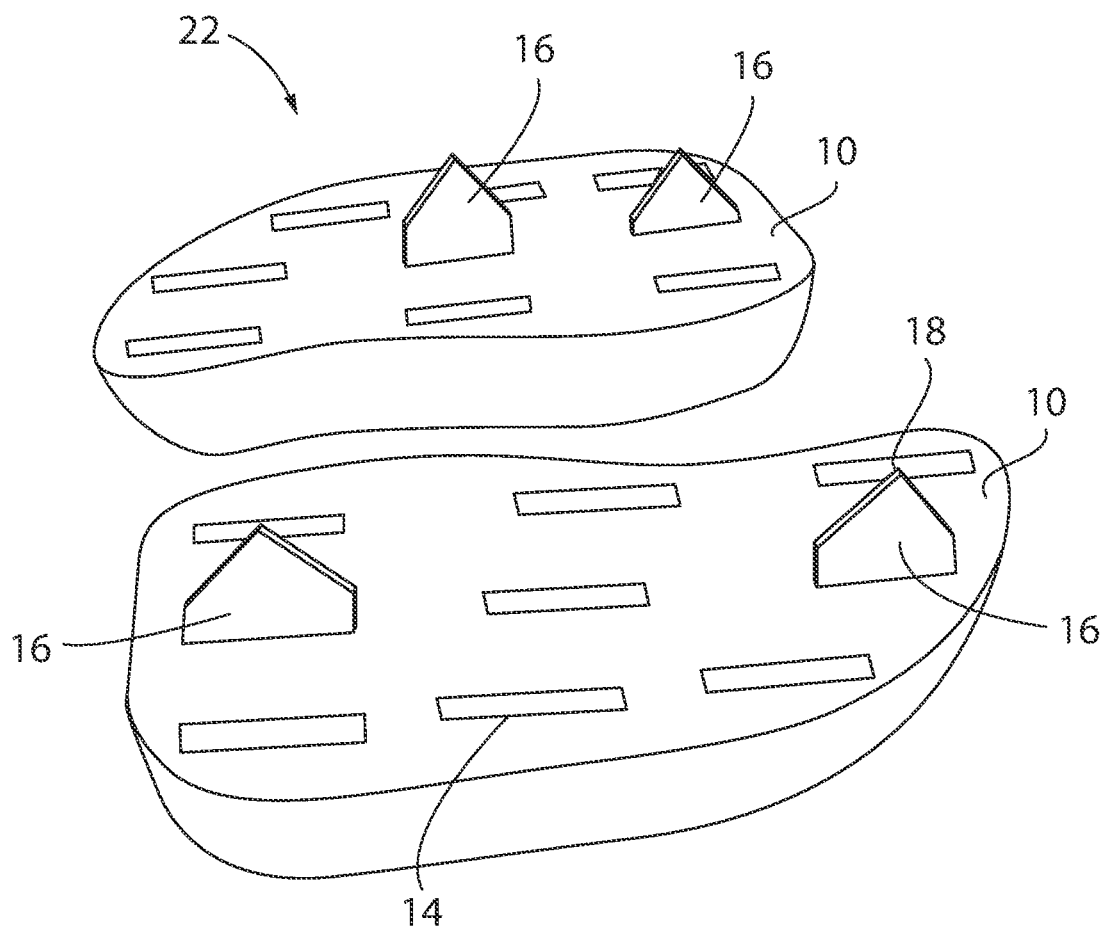
FIG. 5 is a perspective view of the tray mold with inserts inserted therein.

FIGS. 2-4 specifically illustrate three examples of the inserts 16. The inserts 16 preferably include a pointed end 18 and are preferably shaped as an irregularly shaped pentagon, however, other shapes and other ends can also be utilized with the present invention. The inserts 16 have a height and preferably have different heights such as the illustrated 1 mm, 3 mm and 5 mm, in which the stated measurements extend above the plane of the sealed surface. However, it should be noted that different heights can also be utilized. The inserts 16 are designed to be inserted into the slots 14 of the tray mold 10 with the pointed end 18 extending outwardly from the slot 14.

Figure 6:
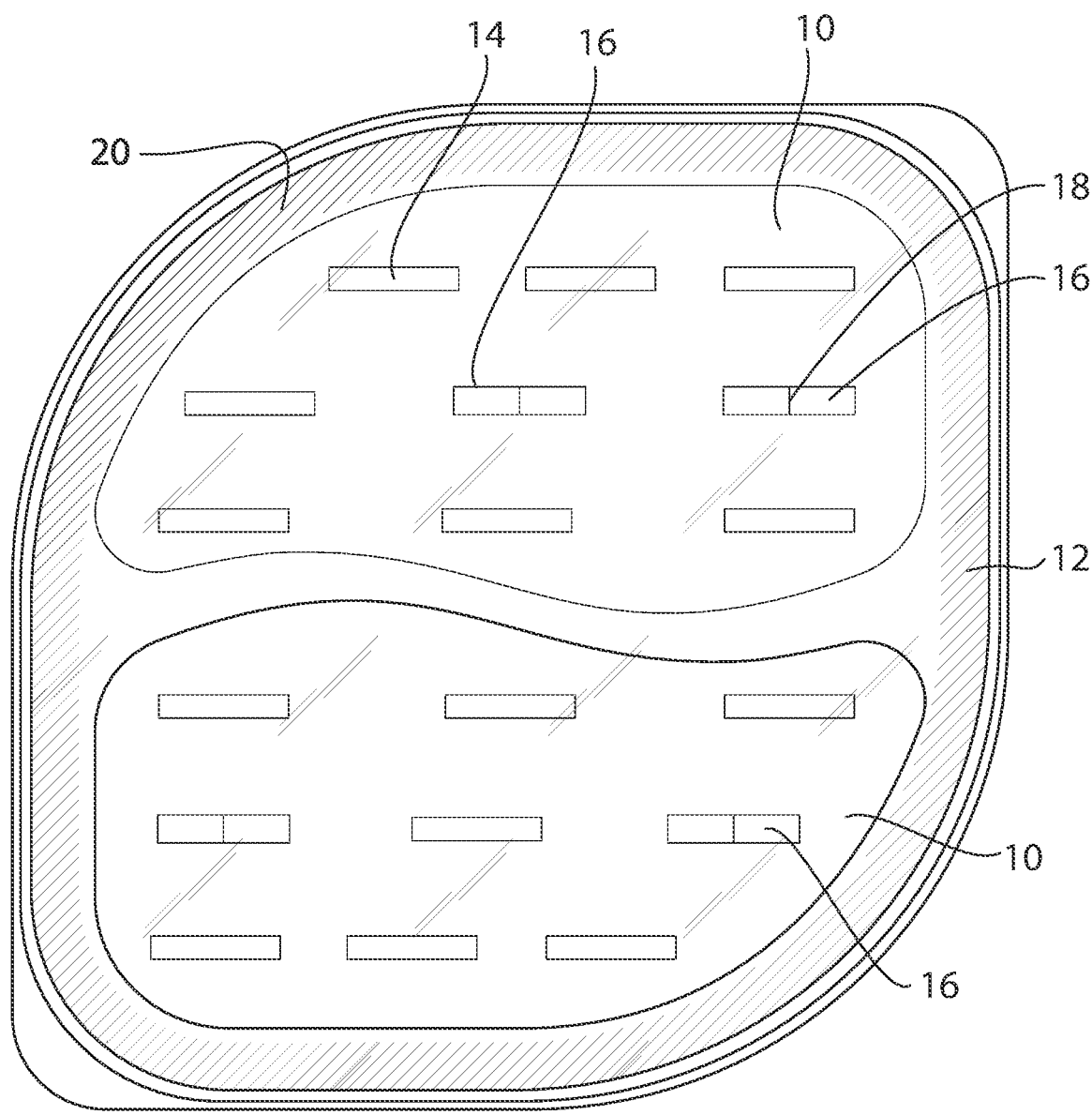
FIG. 6 is a perspective view of the tray mold positioned in a product tray with inserts inserted in the tray mold and a film structure sealed to the product tray.

As shown in FIG. 6, a film structure 20 to be tested can be of varying types of films used in product packaging such as bases structures of PET, Nylon, PP, each of which can exhibit a coextrusion or laminate of sealant and/or combination of other structures or materials to aide in overall performance of the final material. The film structure 20 is secured to the tray 10 or product package 12 by sealing.

The film testing tool 22 includes the tray mold 10 and at least one insert 16. The testing tool 22 is utilized to test a film structure's resistance to puncturing. Specifically, the pointed end 18 of the insert 16 is used to test the film structure's ability to resist being punctured thus causing a leak in the product package 12. Preferably, the inserts 16 are inserted into the tray mold slots 14 with the pointed end 18 upward to simulate a solid item in the product package 12 such as a cracker. The film testing tool 22 allows for consistency in puncture testing across different film structures 20.

Figure 7:
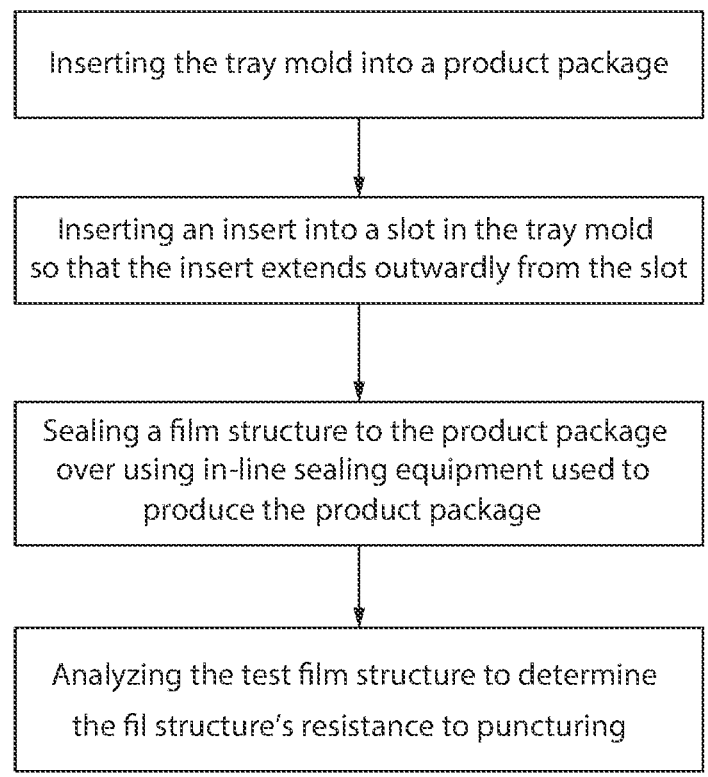
FIG. 7 is a flowchart of a method of the present invention.

In operation and in reference to FIG. 7, the tray mold 10 with one or more inserts 16 therein is placed into the product package 12. One film structure 20 is sealed to the product package 12 to observe the film structure's ability to resist puncturing. For example, in-line sealing equipment that a manufacturer already has in its facility, such as the Mini Mondini available from G. Mondini of Cologne Italy, can be used on a manufacturing line to seal the various film structures 20 to packages 12. However, other off-line or in-line methods can also be used to secure the film structure 20 to the product package 12.

After the film structure is sealed to the product package 12, the film structure can be visually analyzed to determine if the film structure 20 has been punctured and, if so, the puncture severity. The film structure 20 can also be sent to a lab for analysis under a microscope to observe how deep/severe the punctures are.

The puncture testing tool 22 allows for the puncture testing of a variety of film structures 20 in a consistent, comparative, replicable and cost-effective way using sealing equipment that the product package manufacturer already has in its facility.

Since the location of the solid items within the product package 12 can vary, providing multiple slots 14 in the tray mold 10 can provide an opportunity to evaluate potential punctures based on location. For example, the film structure 20 may be less taut in one location as compared to another. Since there may be more than one solid item in the product package 12, providing multiple inserts 16 can provide an opportunity to evaluate greater than one solid item puncturing through the film structure 20.

Various features and advantages of the invention are set forth in the following claims.

What is claimed is:

1. A film puncture testing tool for testing resistance to puncturing of a film structure for a product package, said film puncture testing tool comprising:
    a tray mold insertable into a product package and including one slot; and
    an insert terminating in an end, the insert being positioned in the slot in an orientation with the end extending outwardly of the slot so that a film structure to be tested can be sealed to the product package over the mold and the insert.

2. The film puncture testing tool of claim 1 wherein the tray mold fills the product package.

3. The film puncture testing tool of claim 1 wherein the end of the insert is pointed.

4. The film puncture testing tool of claim 1 wherein the film structure includes one of PET, Nylon or PP type film.

5. The film puncture testing tool of claim 1 wherein the tray mold is 3d printed.

6. A method for testing the resistance of a film structure on product package to puncturing, said method including the steps:
    inserting a tray mold having a slot into a product package;
    inserting an insert into the slot, the insert having a portion that extends outwardly from the slot to simulate a rigid object in the product package; and
    covering the tray mold and the insert with a film structure to be tested.

7. The method of claim 6 wherein the insert has a pointed end that extends outwardly from the slot and wherein the pointed end extends beyond a plane of the covered tray mold.

8. The method of claim 6 wherein the tray mold includes a plurality of slots.

9. The method of claim 8 wherein in the inserting step, a plurality of inserts are inserted into the plurality of slots.

10. The method of claim 6 wherein in the covering step, the film structure is sealed to the product package.

11. A method for analyzing the puncture resistance of a film structure sealed to a product package using a sealer, said method including the steps:
    inserting a tray mold having a slot into a product package, the slot having a height;
    inserting an insert having a height greater than the height of the slot into the slot so that the insert extends outwardly from the slot;
    sealing a film structure to the product package over the mold and the insert using a sealer used to produce the product package; and
    analyzing the test film structure to determine the resistance to puncturing of the film structure.

12. The method of claim 11 wherein the insert has an irregular pentagon shape.

13. The method of claim 12 wherein the insert has a pointed end.

14. The method of claim 11 wherein the film structure to be tested is one of PET, Nylon and PP.

15. The method of claim 11 wherein in the analyzing step, the analyzing is done visually.

16. The method of claim 11 wherein in the analyzing step, the analyzing is done microscopically.

17. A method for testing the resistance of a film structure on product package to puncturing, said method including the steps:
    inserting a tray mold into a product package, the tray mold having at least one insert extending outwardly therefrom to simulate a rigid object in the product package; and
    covering the tray mold and the insert with a film structure to be tested.

* * * * *